US00RE33996E

United States Patent [19]

Jandacek

[11] E Patent Number: Re. 33,996

[45] Reissued Date of Patent: Jul. 14, 1992

[54] COMPOSITIONS FOR TREATING HYPERCHOLESTEROLEMIA

[75] Inventor: Ronald J. Jandacek, Cincinnati, Ohio

[73] Assignee: The Procter & Gamble Company, Cincinnati, Ohio

[21] Appl. No.: 346,662

[22] Filed: May 3, 1989

Related U.S. Patent Documents

Reissue of:

[64] Patent No.: 4,005,195
Issued: Jan. 25, 1977
Appl. No.: 657,528
Filed: Feb. 12, 1976

[51] Int. Cl.[5] ..... A61K 31/23; A61K 31/70

[52] U.S. Cl. ..... 514/23; 514/53; 514/552; 514/558; 514/560

[58] Field of Search ..... 514/552, 558, 23

[56] References Cited

U.S. PATENT DOCUMENTS

| | | |
|---|---|---|
| 1,656,474 | 1/1928 | Dubin . |
| 2,266,591 | 12/1941 | Eckey et al. . |
| 2,831,854 | 4/1958 | Tucker et al. . |
| 2,893,990 | 7/1959 | Hass et al. . |
| 2,962,419 | 11/1960 | Minich . |
| 2,997,491 | 8/1961 | Huber et al. . |
| 2,997,492 | 8/1961 | Martin . |
| 2,997,493 | 8/1961 | Huber . |
| 2,999,023 | 9/1961 | Babayan et al. . |
| 3,059,009 | 10/1962 | Schmid et al. . |
| 3,059,010 | 10/1962 | Schmid et al. . |
| 3,158,490 | 11/1964 | Baur et al. . |
| 3,160,565 | 12/1964 | Duell . |
| 3,351,531 | 11/1967 | Noznick et al. . |
| 3,353,966 | 11/1967 | Hugenberg . |
| 3,353,967 | 11/1967 | Lutton . |
| 3,495,010 | 2/1970 | Fossel . |
| 3,495,011 | 2/1970 | Fossel . |
| 3,597,230 | 8/1971 | Colby et al. . |
| 3,600,186 | 8/1971 | Mattson et al. . |
| 3,849,554 | 11/1974 | Winitz . |
| 3,954,976 | 5/1976 | Mattson et al. . |
| 4,005,196 | 1/1977 | Jandacek et al. . |
| 4,034,083 | 7/1977 | Mattson . |

FOREIGN PATENT DOCUMENTS

| | | |
|---|---|---|
| 2458732 | 6/1975 | Fed. Rep. of Germany . |
| 2254318 | 7/1975 | France . |

OTHER PUBLICATIONS

Swern-Bailey's Industrial Oil and Fat Products 3rd edit. (1964) John Wiley and Sons, p. 179.

Fallat et al., "Sucrose Polyester: A cholesterol Lowering, Noncaloric, Unabsorbable Synthetic, Fat Food Additive," Clinical Research, vol. 23, p. 319A (1975).

Mattson et al., "Absorbability by Rats of Compounds Containing from 1 to 8 Ester Groups," J. Nutr. vol. 102, pp. 1171-1176 (1972).

Mattson et al., "Rate and Extent of Absorption of the Fatty Acids of Fully Esterified Glycol, Erythritol, etc.," J. Nutr., vol. 102, pp. 1177-1178.

Mattson, "The Absorbability of Stearic Acid When Fat is a Simple or Mixed Triglyceride," J. Nutr., vol. 69, pp. 338-342 (1959).

Deuel, The Lipids, vol. II: Biochemistry (1955), pp. 215 and 227-231.

Mattson et al., "The Digestion and Absorption of Triglycerides," J. Biol. Chem., vol. 239, pp. 2772-2777 (1964).

Lutton, "Lipid Structures," J. Am. Oil Chem. Soc., vol. 49, pp. 109 (1972).

*Primary Examiner*—Sam Rosen

*Attorney, Agent, or Firm*—Eric W. Guttag; Ronald L. Hemingway; Richard C. Witte

[57] ABSTRACT

Anti-anal leakage agents are used in combination with liquid polyol fatty acid polyesters to provide pharmaceutical and food compositions for treating and/or preventing hypercholesterolemia while avoiding undesired anal leakage of the liquid polyesters.

76 Claims, No Drawings

COMPOSITIONS FOR TREATING HYPERCHOLESTEROLEMIA

Matter enclosed in heavy brackets [ ] appears in the original patent but forms no part of this reissue specification; matter printed in italics indicates the additions made by reissue.

BACKGROUND OF THE INVENTION

The present invention relates to certain edible, but non-absorbable and non-digestible, liquid polyesters which can be used as low calorie fat substitutes in foods and as pharmaceutical compositions. The polyesters herein interfere with the body's absorption of cholesterol and thereby provide a means for treating hypercholesterolemia. It has now been determined that the liquid polyesters herein can also cause an undesired anal leakage effect. By the present invention, certain agents are added to the polyester compositions to avoid this undesired effect. Highly preferred compositions for treating hypercholesterolemia and/or hyperlipidemia comprising the polyesters and anti-anal leakage agent are provided.

High blood cholesterol (hypercholesterolemia) is recognized as being a risk factor in cardiovascular disease which comprises a major health care problem today. Epidemiological studies have demonstrated that, with few exceptions, populations consuming large quantities of saturated fat and cholesterol have a relatively high concentration of serum cholesterol and a high mortality rate from coronary heart disease. While it is recognized that other factors can also contribute to the development of cardiovascular disease, there appears to be a causal relationship between the concentration of serum cholesterol, in which hypercholesterolemia results in the accumulation of undesirable amounts of cholesterol in various parts of the circulatory system (atherosclerosis) or in soft tissues (xanthomatosis), and coronary disease and coronary mortality rates.

A variety of dietary and drug regimens have been suggested for alleviating or preventing hypercholesterolemia.

By providing a fat substitute which is non-absorbable and non-digestible, the total content of cholesterol in the body can be lowered. Mineral oil is a well-known laxative and has been suggested for use as a fat substitute and as a kind of "intestinal solvent" to dissolve cholesterol and cause its removal in body wastes. However, mineral oil has never been accepted for these uses. Moreover, mineral oil is partially absorbed by the body and undesirably deposits in the liver.

In the present invention, liquid, non-absorbable, non-digestible polyesters of sugars (or sugar alcohols) are used as fat substitutes in foods and, conveniently, in unit dose forms as therapeutic compositions. The polyesters herein are fat-like in their physical properties and are excellent fat substitutes for use in low calorie foods and diets. Moreover, the polyesters herein efficiently inhibit absorption of cholesterol by the body and, in contrast with mineral oil, are not absorbed and/or deposited in the liver during usage in a treatment/prevention regimen with persons having or likely to develop hypercholesterolemia.

The anal leakage effect of the liquid polyesters of the type disclosed herein can be overcome by adding an anti-anal leakage agent of the type disclosed hereinafter to the liquid polyesters, or to foods containing same.

The following references are relevant to the present invention.

The copending application of Mattson, Ser. No. 628,265, filed Nov. 3, 1975, entitled COMPOSITIONS FOR INHIBITING ABSORPTION OF CHOLESTEROL, discloses vitamin-fortified liquid and solid polyesters of the general type employed herein, their use as anti-hypercholesterolemic and anti-hyperlipidemic agents, and their stool-softening laxative effect.

The concurrently-filed application of Jandacek and Mattson, Ser. No. 657,529, filed Feb. 12, 1976, P&G Attorney's Docket No. 2309, entitled VITAMINIZED COMPOSITIONS FOR TREATING HYPERCHOLESTEROLEMIA, discloses ternary compositions comprising fat-soluble vitamins, anti-anal leakage agents and a liquid polyester of the type employed herein.

U.S. Pat. No. 3,600,186 (1971) to Mattson and Volpenhein discloses low calorie food compositions containing polyol polyesters of the general type employed herein, and their use in combination with hardstocks which are fatty acid sources. The anti-anal leakage effect of fatty acids is not noted.

The copending application of Mattson and Volpenhein, entitled PHARMACEUTICAL COMPOSITIONS FOR INHIBITING ABSORPTION OF CHOLESTEROL, Ser. No. 425,010, filed Dec. 14, 1973, now U.S. Pat. No. 3,954,976 discloses and claims sugar polyesters of the general type employed herein for the treatment and/or prevention of hypercholesterolemia. A variety of optional carriers are mentioned, including the fatty acid, stearic acid. The anti-anal leakage effect of stearic acid is not mentioned.

U.S. Pat. No. 1,656,474 (1928) to Dubin discloses edible fat compositions consisting of ethyl and glycerol esters of odd chain fatty acids in combination with fat-soluble vitamins.

Mattson and Nolen, The Journal of Nutrition Vol. 102, No. 9, September 1972, at pages 1171–1175, report on the lack of absorbability of sugar polyesters of the general type employed herein in rats.

Fallet, Glueck, Mattson and Lutmer, Clinical Research XXIII No. 3, page 319A (1975) report the lowering of both serum cholesterol and vitamin A and E levels in subjects receiving sugar polyesters of the present type.

U.S. Pat. No. 2,962,419 (1960) to Minich relates to neopentyl fatty esters and their use as fat substitutes.

U.S. Pat. No. 3,160,565 (1964) to H. E. Duell relates to sugar mono-, di- and tri-esters and their use as carriers for varying orally-administered medicinals.

U.S. Pat. No. 3,849,554 (1974) to Winitz discloses means for reducing blood serum cholesterol by injesting diets comprising a fatty acid source, said diets being low in sucrose.

U.S. Pat. No. 2,893,990 (1959) to Hass, et al., discloses fatty acid mono- and di-esters of sucrose which aid in the absorption of fat from the digestive tract.

U.S. Pat. No. 3,158,490 (1964) to Baur and Lutton discloses non-cloudy salad oils containing esters of disaccharides in which there are not more than five unesterified hydroxy groups. See also U.S. Pat. Nos. 3,059,009 (1962) and 3,059,010 (1962) to Schmid and Baur.

U.S. Pat. No. 2,997,492 (1961) to Martin is directed to a method of making partial fatty acid esters of hexitols. U.S. Pat. No. 2,997,491 (1961) to Huber is directed to the synthesis of partial fatty esters of inositol. The general methods of synthesis disclosed in these patents can be used to prepare the liquid polyesters herein. Preferred methods of synthesis are fully disclosed hereinafter.

SUMMARY OF THE INVENTION

Administration of anti-hypercholesterolemic amounts of a composition comprising a liquid polyester of the type described herein to an animal (especially humans) afflicted with or susceptible to hypercholesterolemia is an effective means of controlling the body's cholesterol level. Unfortunately, administration of cholesterol-controlling amounts of the liquid polyesters can result in an undesired "laxative" effect, namely, leakage of the liquid polyester through the anal sphincter. By combining the polyester compositions with an anti-laxative agent, especially a $C_{12}$, or higher, saturated fatty acid, or edible source which provides such fatty acids in the gut, this undesired laxative effect is prevented. (By "anti-anal leakage agent", or "AAL" agent, herein is meant those materials which prevent frank leakage of the liquid polyesters. The natural stool-softening effect of the polyesters is not substantially affected, nor is it a problem.)

The present invention encompasses compositions of matter which comprise a liquid, non-absorbable, nondigestible polyol fatty acid polyester of the type described hereinafter, and an anti-laxative, or "stiffening", amount of an anti-laxative agent, especially sources of $C_{12}$, or higher, fatty acids. The compositions can be used as fat substitutes in cooking or can be self-administered to reduce the body's cholesterol level. Such compositions also find use as diet aids for the hyperlipidemic individual.

The present invention also encompasses non-laxative pharmaceutical compositions in effective unit dosage amounts for inhibiting the absorption of cholesterol, said compositions comprising from about 1 gram to about 5 grams of the liquid polyesters herein and sufficient AAL agent, especially a $C_{12}$, or higher, saturated fatty acid, or edible source thereof, to prevent anal leakage in humans ingesting said compositions.

The polyester materials herein are non-absorbable and non-digestible fat-like materials and are suitable for use as fat substitutes in low calorie fat-containing food compositions. Accordingly, the present invention also encompasses low calorie fat-containing food compositions comprising non-fat ingredients and fat ingredients wherein from about 10% to about 100% of the total fat ingredients comprise the liquid, non-absorbable, nondigestible polyesters of the type disclosed hereinafter, said compositions also containing an effective amount of an AAL agent, especially a $C_{12}$, or higher, saturated fatty acid, or an edible source of fatty acids, which prevents an undesired anal leakage effect.

The present invention also encompasses methods for inhibiting the absorption of cholesterol without causing an anal leakage effect, comprising systemically (generally, orally) administering to animals susceptible to or afflicted with hypercholesterolemia successive therapeutically effective doses of the compositions of the foregoing type.

It is to be understood that the edible, non-absorbable, non-digestible polyester materials herein are liquids at body temperature, i.e., have a melting point of ca. 37° C. or below. (Edible, non-absorbable, non-digestible polyester materials that are solid at body temperature do not exhibit the undesirable anal leakage effects noted with the liquid polyesters. Indeed, such solid polyesters can be used as one type of AAL agent herein.) In general, the liquid polyesters are those which are made from unsaturated fatty acids, whereas the solid polyesters are substantially saturated.

DETAILED DESCRIPTION OF THE INVENTION

The consumption of diets containing sucrose polyesters (SPE) has been shown to result in the desirable decrease in absorption of dietary cholesterol in animals; see Mattson, Mandacek and Glucek, Clinical Research 23 445A (1975). Similar results have been noted in humans.

In studies of the foregoing type, rats which ingested about 300 mg. to about 3000 mg. total liquid polyester per day and human volunteers who ingested from about 10 grams to about 50 grams total liquid polyester per day exhibited undesired anal leakage of the polyesters. Further studies indicated that this anal leakage effect was a direct result of the passage of the polyesters through the anal sphincter. Briefly, this undesired effect is not unlike the effect which can be caused by the ingestion of excessive amounts of mineral oil. It has now been determined that this undesirable effect can be obviated by combining the liquid polyester compositions with certain AAL agents.

The types of AAL agents which can be used herein to overcome the above-described anal leakage problem without interfering with the beneficial effects of the present compositions are disclosed immediately hereinafter.

Anti-Anal Leakage Agents

One class of materials which provide the anti-anal leakage effect herein includes fatty acids having a melting point of ca. 37° C., or higher, and ingestible, digestible sources of such fatty acids. The fatty acid AAL agents include, for example, the $C_{12}$–$C_{24}$ saturated fatty acids, and ingestible, digestible sources thereof.

While not intending to be limited by theory, it appears that the foregoing type of AAL agent functions via the formation of calcium or magnesium fatty acid soaps in the gut. These soaps apparently interact with the liquid polyesters herein and impart a "stiffening" effect thereto. Once "stiffened", or partly solidified, in the gut, the polyesters do not leak through the anal sphincter. The antihypercholesterolemic effect of the liquid polyesters is not diminished.

Non-limiting examples of saturated fatty acids and sources thereof which can be used as the AAL agent herein include the free saturated fatty acids per se, compounds such as esters (e.g., triglycerides) that yield such saturated fatty acids on hydrolysis in the gut, soaps of the fatty acids such as the sodium, potassium, etc., water-soluble soaps, as well as the calcium and magnesium water-insoluble soaps.

Highly preferred herein for their anti-anal leakage effect are the $C_{16}$–$C_{22}$, most preferably $C_{16}$–$C_{18}$, saturated fatty acids, or edible sources thereof.

Specific examples of materials useful as the foregoing type of AAL agent herein include natural or processed fats yielding $C_{12}$–$C_{24}$ saturated fatty acids in the gut, e.g., materials such as cocoa butter, palm oil, palm kernel oil, coconut oil, tallow, lard, enriched concentrates of triglycerides having high levels of saturated fatty acids obtainable from these sources and sources such as highly saturated cottonseed oil fractions obtained by processes such as crystallization or directed rearrangement which yield the desired higher concentrations of the more saturated fatty acids in the resulting "hardstock" fractions. Such materials are all available by well-known processes.

Partially hydrogenated oils, including all of the above, as well as partially hydrogenated soybean oil, safflower seed oil, rapeseed oil, or such materials which are hydrogenated and concentrated, for example by crystallization, to provide fractions which are enriched in sources of the longer-chain, substantially saturated fatty acids, are all useful as the AAL agent herein. (By "substantially hydrogenated" herein is meant oils having an iodine value of ca. 50, or lower.)

Of course, any of the foregoing unsaturated oils are useful herein after they have been substantially completely hydrogenated to convert the unsaturated fatty acid (ester) groups to the corresponding saturated fatty acids.

Synthetic materials, especially fatty acid esters made from the $C_{12}$–$C_{24}$, more preferably $C_{16}$–$C_{22}$, most preferably $C_{16}$–$C_{18}$, saturated fatty acids are useful herein. Such materials include the esters of tetrahydric alcohols such as erythritol, esters of pentahydric alcohols such as xylitol, and esters of hexahydric alcohols such as sorbitol, and the like.

The $C_{12}$–$C_{24}$ saturated fatty acid esters of monohydric alcohols such as methyl, ethyl and propyl alcohols (preferably ethyl alcohol) are also useful herein. Esters of dihydric alcohols such as 1,2-propanediol, 1,3-butanediol, and the like, can also be used.

Highly preferred AAL agents herein which yield the foregoing fatty acids on hydrolysis in the gut are those which, in combination with the liquid polyesters herein, provide compositions having aesthetically pleasing organoleptic qualities, i.e., better "mouth feel". Such aesthetically pleasing materials include naturally occurring cocoa butter and various synthetic cocoa and confectioners' butters. These preferred AAL agents include, for example, the so-called "position-specific" triglycerides such as 1-stearoyl diolein (SOO); 2-oleoyl-1,3-distearin (SOS); or the corresponding compounds wherein the stearoyl group is replaced by palmitoyl, arachidoyl or behenoyl groups. Another class of aesthetically preferred anti-laxative agents herein are 1-oleoyl distearin (OSS), 1-palmitoyl distearin (PSS), 1-arachidoyl distearin (ASS) and 1-behenoyl distearin (BSS).

These highly preferred, position-specific triglycerides which can be used as a fatty acid source-type of AAL agent herein can be prepared according to the methods described in U.S. Pat. No. 3,809,711, Yetter, issued May 7, 1974, the disclosures of which are incorporated herein by reference.

As noted hereinabove, the foregoing types of AAL agents appear to function by providing a saturated fatty acid in the gut, said fatty acid thereafter presumably forming an insoluble calcium or magnesium soap in situ. This soap then appears to provide the "stiffening" effect on the liquid polyester, thereby preventing the undesirable anal leakage effect. As noted hereinabove, the solid polyester materials of the present type (i.e., solid, edible, but non-digestible, non-absorbable polyesters) do not cause the undesirable anal leakage effect. It has been determined that these solid polyester materials can also be used as an AAL agent and these represent a second class of AAL agents herein. Since these solid polyester materials do not hydrolyze in the gut to form free fatty acids, or calcium or magnesium fatty acid soaps, their anti-anal leakage effect must be the result of a different mechanism from that which operates with the hydrolyzable esters and fatty acid sources described immediately hereinabove. Presumably, the combination of the solid polyester with the liquid polyesters simply provides a stiffening effect due to some type of crystallization or phase change within the gut.

It will be appreciated that by combining liquid and solid non-absorbable, non-digestible polyesters to provide the desired anti-anal leakage effect, wholly edible, but non-digestible, non-absorbable, non-caloric compositions are secured. These compositions are quite effective in the treatment of hypercholesterolemia and in low calorie diets.

Typical examples of solid, non-absorbable, non-digestible polyester AAL agents herein include sucrose octastearate, sucrose octapalmitate, sucrose heptastearate, xylitol pentastearate, galactose pentapalmitate, and like, saturated polyol polyesters having at least four —OH groups esterified with $C_{10}$–$C_{22}$ saturated fatty acids.

Another type of AAL agent herein comprises fatty acid esters which are non-digestible by virtue of branching on the $\alpha$-carbon atom of the fatty acid moiety. Such materials, which are well known in the chemical arts, include, for example, $\alpha$-methyl and $\alpha,\alpha$-dimethyl $C_{10}$–$C_{18}$ fatty acid esters of lower alcohols such as ethanol and of polyols such as glycerol.

LIQUID POLYESTERS

The liquid polyol polyesters (or simply, polyesters) employed in this invention comprise certain polyols, especially sugars or sugar alcohols, esterified with at least four fatty acid groups. Accordingly, the polyol starting material must have at least four esterifiable hydroxyl groups. Examples of preferred polyols are sugars, including monosaccharides and disaccharides, and sugar alcohols. Examples of monosaccharides containing four hydroxyl groups are xylose and arabinose and the sugar alcohol derived from xylose, which has five hydroxyl groups, i.e., xylitol. (The monosaccharide, erythrose, is not suitable in the practice of this invention since it only contains three hydroxyl groups, but the sugar alcohol derived from erythrose, i.e., erythritol, contains four hydroxyl groups and accordingly can be used.) Suitable five hydroxyl group-containing monosaccharides are galactose, fructose, and sorbose. Sugar alcohols containing six —OH groups derived from the hydrolysis products of sucrose, as well as glucose and sorbose, e.g., sorbitol, are also suitable. Examples of disaccharide polyols which can be used include maltose, lactose, and sucrose, all of which contain eight hydroxyl groups.

Preferred polyols for preparing the polyesters for use in the present invention are selected from the group consisting of erythritol, xylitol, sorbitol, glucose and sucrose. Sucrose is especially preferred.

The polyol starting material having at least four hydroxyl groups must be esterified on at least four of the —OH groups with a fatty acid containing from about 8 to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers. However, in order to provide liquid polyesters of the type used herein, at least about half of the fatty acid incorporated into the polyester molecule must be unsaturated. Oleic and linoleic acids, and mixtures thereof, are especially preferred.

The liquid polyol fatty acid polyesters useful in this invention must contain at least four fatty acid ester groups. Polyol fatty acid polyester compounds that contain three or less fatty acid ester groups are digested in and the products of digestion are absorbed from the intestinal tract much in the manner of ordinary triglyceride fats, whereas the polyol fatty acid polyester compounds that contain four or more fatty acid ester groups are substantially non-digestible and consequently non-absorbable by the human body. It is not necessary that all of the hydroxyl groups of the polyol be esterified with fatty acid, but it is preferable that the polyester contain no more than two unesterified hydroxyl groups. Most preferably, substantially all of the hydroxyl groups of the polyol are esterified with fatty acid, i.e., the compound is substantially completely esterified. The fatty acids esterified to the polyol molecule can be the same or mixed (but, as noted above, a substantial amount of the unsaturated acid ester groups must be present to provide liquidity).

To illustrate the above points, a sucrose fatty triester would not be suitable for use herein because it does not contain the required four fatty acid ester groups. A sucrose tetra-fatty acid ester would be suitable, but is not preferred because it has more than two unesterified hydroxyl groups. A sucrose hexa-fatty acid ester would be preferred because it has no more than two unesterified hydroxyl groups. Highly preferred compounds in which all the hydroxyl groups are esterified with fatty acid include the liquid sucrose octa-fatty acid esters.

The following are non-limiting examples of specific liquid polyol fatty acid polyesters containing at least four fatty acid ester groups suitable for use in the present invention: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoleate, sucrose hexaoleate, sucrose heptaoleate, sucrose octaoleate, and mixtures thereof.

As noted above, highly preferred polyol fatty acid esters are those wherein the fatty acids contain from about 14 to about 18 carbon atoms.

The polyol fatty acid polyesters suitable for use herein can be prepared by a variety of methods well known to those skilled in the art. These methods include: transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. As an example, the preparation of polyol fatty acid esters is described in U.S. Pat. No. 2,831,854, incorporated herein by reference.

Specific, but non-limiting, examples of the preparation of polyol fatty acid esters suitable for use in the practice of this invention are as follows.

Erythritol tetraoleate — Erythritol and a five-fold molar excess of methyl oleate are heated at 180° C., under vacuum, with agitation, in the presence of sodium methoxide catalyst over two reaction periods of several hours each. The reaction product (predominately erythritol tetraoleate) is refined in petroleum ether and crystallized three times from several volumes of acetne at 1° C. acetone Xylitol pentaoleate — Xylitol and a five-fold molar excess of methyl oleate in dimethylacetamide (DMAC) solution are heated at 180° C. for five hours in the presence of sodium methoxide catalyst, under vacuum. During this time the DMAC is removed by distillation. The product (predominately xylitol pentaoleate) is refined in petroleum ether solution and, after being freed of petroleum ether, is separated as a liquid layer four times from acetone at ca. 1° C. and twice from alcohol at ca. 10° C.

Sorbitol hexaoleate is prepared by essentially the same procedure used to prepare xylitol pentaoleate except that sorbitol is substituted for xylitol.

Sucrose octaoleate is prepared by substantially the same procedure as that used to prepare erythritol tetraoleate except that sucrose is substituted for erythritol.

In therapeutic regimens the dosage of the compositions herein can vary with the severity of the hypercholesterolemic condition and the duration of the treatment. Individual dosages can range from about 0.01 mg./kg. to about 500 mg./kg., and greater (unless otherwise specified, the unit designated "mg./kg." as used herein refers to mg. of liquid polyester per kilogram of body weight), preferably from about 0.1 mg./kg. to about 125 mg./kg. per dosage, with up to six dosages, preferably three dosages, being given daily, most preferably at meal times. Because of the AAL agent, such high dosages can be administered without fear of producing anal leakage effects. Dosages of less than about 0.1 mg./kg. do not materially inhibit the absorption of cholesterol in most patients. The dosages can be administered orally in any suitable unit dosage form such as pills, tablets, and capsules. Preferred are capsules made from gelatin. The dosages can also be administered as part of a controlled dietary regimen, e.g., as a synthetic salad oil or cooking oil or fat.

The pharmaceutical compositions herein can comprise the polyester/AAL agent alone, or in combination with any desired, non-interfering pharmaceutical carrier. As used herein, the term "pharmaceutical carrier" means a solid or liquid filler, diluent or encapsulating substance. Some examples of the substances which can serve as pharmaceutical carriers are sugars such as lactose, glucose and sucrose; starches such as corn starch and potato starch; cellulose and its derivatives such as sodium carboxymethylcellulose, ethylcellulose, cellulose acetate; powdered tragacanth; malt; gelatin; talc; oils such as peanut oil, cottonseed oil, sesame oil, olive oil, corn oil and soybean oil; polyols such as propylene glycol, glycerin, sorbitol, mannitol, and polyethylene glycol; agar; alginic acid; pyrogen-free water; isotonic saline; ethyl alcohol and phosphate buffer solutions, as well as other non-toxic compatible substances used in pharmaceutical formulations. Wetting agents and lubricants such as sodium lauryl sulfate, as well as coloring agents, flavoring agents and preservatives can also be present in the compositions, according to the desires of the formulator.

The pharmaceutical carriers of the foregoing type can optionally be employed in conjunction with the liquid polyesters herein to provide a practical size to dosage relationship, composition forms which can be easily ingested, and means for providing accurate unit dosages in a convenient form. The pharmaceutical carrier usually will comprise from about 5% to about 50% by weight of the total pharmaceutical composition.

Since the liquid polyesters of the present compositions are not unlike cooking and salad oils and fats in their physical properties, the present compositions can be used as a partial or total replacement for normal triglyceride fats in any fat-containing food composition to provide anti-hypercholesterolemic and low calorie benefits. In order to achieve these benefits in a reasonable time, it is necessary that at least about 10% of the fat in the food composition comprises the polyesters herein. Highly desirable food compositions are those wherein the fatty component comprises up to about 100% of the polyester/anti-anal leakage compositions herein. Accordingly, the compositions of this invention can be used as a partial or complete replacement for normal triglyceride fats in a salad or cooking oil, or in plastic shortenings for use in frying, cake making, bread making, and the like. The compositions can also be used as partial or complete replacements for normal triglyceride fats in fat-containing food products such as mayonnaise, margarine, and dairy products.

Preferred fat-containing food compositions of the present type comprise non-fat ingredients and fat ingredients wherein from about 10% to about 95% of the total fat consists essentially of a liquid sugar fatty acid polyester having at least four fatty acid ester groups, each fatty acid having from about 8 to about 22 carbon atoms, said sugar fatty acid polyester and/or food composition made therefrom also comprising an AAL agent of the type disclosed herein. Such food compositions will most often contain at least about 10%, generally 15% to 25% (by weight of liquid polyester) of a fatty acid source which provides the anti-anal leakage effect. Highly preferred are food compositions wherein the sugar fatty acid ester contains no more than two unesterified hydroxyl groups. Liquid sucrose polyesters, especially those wherein the ester groups are mainly of the unsaturated type and contain 14 to 18 carbon atoms, when used in the manner of this invention, are especially preferred for use in such anti-hypercholesterolemic and low calorie food compositions.

The total AAL agent employed in any of the compositions and methods herein will depend somewhat on the total amount of liquid polyester being ingested per day. The anti-anal leakage agent should be present in an amount equaling at least about 10% by weight of the liquid polyester. It is more preferred that the AAL agent comprises at least about 20% by weight of the liquid polyester to ensure that anal leakage does not, even at high ingestion rates. Compositions wherein the weight of AAL agent comprises from about 20% to about 50% of the weight of liquid polyester provide excellent control of serum cholesterol without anal leakage of the polyester.

Compositions comprising edible fatty acids, their edible salts or their edible, digestible esters as the AAL agent preferably comprise about 10% to about 50% by weight of these materials by weight of liquid polyester. Compositions using the palatable position-specific triglycerides as the AAL agent preferably comprise about 20% to about 40% (by weight of liquid polyester) of these AAL agents. When the edible, non-absorbable, non-digestible solid polyesters are used as the AAL agent, they are preferably used at a rate of from about 20% to about 50% by weight of the liquid polyester.

The following, non-limiting examples illustrate the compositions and processes of this invention. It will be appreciated that sugars and sugar alcohols, appropriately esterified, are encompassed by the term "sugar" as used herein and such materials can be interchanged in the compositions.

EXAMPLE I

Gelatin capsules for use by the hypercholesterolemic patient are prepared by conventional methods, as follows:

| Ingredient | Amount per Capsule |
|---|---|
| Sucrose polyester* | 2000 mg. |
| Stearic Acid | 250 mg. |

*Liquid mixed hexa-, hepta- and octa-sucrose esters, predominately the octa-ester, esterified with mixed soybean oil fatty acids, predominately in the $C_{16}$–$C_{18}$ chain length.

The capsules of the foregoing type are prepared by simply mixing the ingredients and filling the standard gelatin capsules. The capsules are administered orally three times daily (three with each meal). This treatment regimen inhibits cholesterol uptake significantly and decreases the serum cholesterol levels in the circulatory systems of humans with, or disposed towards, hypercholesterolemia. The patients are not troubled by undesired anal leakage with this regimen.

Similar results are obtained when the sucrose polyester in the capsules of Example I is replaced with an equivalent quantity of a fatty acid polyester selected from the group consisting of glucose tetraoleate; glucose tetraoleate; mixed glucose tetraesters of unsaturated soybean oil fatty acids; mixed mannose tetraesters of oleic acid; mixed galactose tetraesters of linoleic acid; mixed arabinose tetraesters of oleic acid; xylose tetralinoleate; galactose pentaoleate; sorbitol tetraoleate; sucrose tetraoleate; sucrose pentaoleate; sucrose hexaoleate; sucrose heptaoleate; and sucrose octaoleate, respectively.

In the composition of Example I, the stearic acid anti-anal leakage ingredient is replaced by an equivalent amount of methyl stearate, propyl stearate, methyl behenate, ethyl behenate, substantially completely hydrogenated palm oil, hydrogenated rapeseed oil, and mixed hydrogenated tallow triglycerides, respectively, and equivalent results are secured.

Preferred pharmaceutical compositions of the type of Example I for inhibiting the absorption of cholesterol, especially in the human body, preferably comprise from about 0.1 gram to about 5 grams of the liquid polyester and an effective amount (as disclosed hereinabove) of the AAL agent.

EXAMPLE II

Gelatin capsules comprising a unit dose of an AAL agent and a liquid polyester are prepared by conventional means, as follows:

| Ingredient | Amount per Capsule |
|---|---|
| Sucrose octaoleate | 3500 mg. |
| Hydrogenated palm oil | 750 mg. |

The above capsules are administered orally three times daily (three per meal/70 kg. man) over a one-month period. This treatment regimen substantially inhibits cholesterol uptake in the patient and decreases the serum level of cholesterol. No anal leakage from use of the capsules is noted.

The hydrogenated palm oil in Example II is replaced by an equivalent amount of tristearin and equivalent anti-anal leakage results are secured.

When oleic acid is used to replace the hydrogenated palm oil, no substantial anti-anal leakage effect is noted.

EXAMPLE III

Gelatin capsules comprising an AAL agent and a liquid polyester are as follows:

| Ingredient | Mg. per Capsule |
|---|---|
| Sucrose octaoleate | 2000 |
| Ethyl stearate | 250 |

Three capsules of the type prepared in Example III are administered orally five times daily (three capsules per occurrence) to inhibit cholesterol uptake and decrease the level of cholesterol in the circulatory system of a 70 kg. patient afflicted with hypercholesterolemia. At these dosage levels, no anal leakage is noted. Similar dosages of the foregoing capsules without ethyl stearate cause an undesired leakage of sucrose octaoleate through the anal sphincter.

EXAMPLE IV

A highly palatable, low calorie composition suitable for use by patients on anti-hypercholesterolemic therapeutic regimens and/or as a cooking fat substitute by individuals on an anti-hyperlipidemic diet is as follows:

| Ingredient | % by Weight |
|---|---|
| Liquid sucrose polyester* | 50 |
| Cocoa butter | 50 |

*Avg. 7.5 ester of sucrose and oleic acid.

The composition of the foregoing type is suitable for use in standard fashion as a low calorie cooking fat. No anal leakage of the liquid polyester is noted.

The composition of Example IV is ingested at a rate of 50 g./day (150 lb. patient) and reduces serum cholesterol without anal leakage of the liquid polyester.

In the composition of Example IV the natural cocoa butter is replaced by an equivalent amount of the position-specific triglycerides SOO, SOS, OSS, PSS, ASS and BSS, respectively, and equivalent compositions are secured.

EXAMPLE V

A plastic shortening is prepared from the following ingredients.

| Ingredient | % by Weight |
|---|---|
| Cocoa butter | 40 |
| Liquid xylitol pentaoleate | 50 |
| OSS | 10 |

The composition of Example V is prepared by thoroughly mixing the indicated ingredients. The composition is suitable for use in frying and other types of cooking where a plastic fat is employed. The fat composition of Example V can also be employed in the preparation of baking doughs suitable for use by the hypercholesterolemic patient. Continued ingestion of the plastic shortening of Example V, or foods made therefrom, reduces the body's serum cholesterol level without anal leakage of the xylitol pentaoleate.

The shortening of Example V can be used by the normal or hyperlipidemic patient to control body weight.

EXAMPLE VI

A non-anal leakage, low calorie, anti-hypercholesterolemic composition prepared with an edible, but non-absorbable, non-digestible, solid polyester AAL agent is as follows:

| Ingredient | % by Weight |
|---|---|
| Sucrose octaoleate | 70 |
| Sucrose octastearate | 30 |

The composition of Example VI is prepared by simply combining the ingredients. The composition is suitable for use by the hypercholesterolemic patient to reduce serum cholesterol levels; no anal leakage is noted.

The composition of Example VI can be used by the normal or hyperlipidemic patient to control serum cholesterol without increasing caloric intake.

In the composition of Example VI the sucrose octastearate is replaced by an equivalent amount of sucrose heptastearate, and sucrose octapalmitate, respectively, as the AAL agent and equivalent results are secured.

What is claimed is:

1. A composition of matter, comprising:

(a) an edible, non-absorbable, non-digestible liquid polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and (b) sufficient anti-anal leakage agent to prevent leakage of said liquid polyester through the anal sphincter, *wherein the anti-anal leakage agent is a member selected from the group consisting of: edible $C_{12}$ and higher saturated fatty acids, and their edible salts; edible, digestible sources of $C_{12}$ and higher saturated fatty acids, other than tristearin or $C_{18}$ saturated fatty acid esters of 1,3-propanediol; edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group is a saturated fatty acid group having from about 8 to about 22 carbon atoms; and edible, non-digestible esters of alpha-branched chain $C_{10}$–$C_{18}$ fatty acids.*

2. A composition according to claim 1 wherein the liquid polyol fatty acid polyester contains no more than about 2 free hydroxyl groups.

3. A composition according to claim 2 wherein the fatty acid ester groups contain from about 14 to about 18 carbon atoms.

4. A composition according to claim 3 wherein the polyol is a member selected from the group consisting of erythritol, xylitol, sorbitol, glucose and sucrose.

[5. A composition according to claim 4 wherein the polyol is sucrose.]

[6. A composition according to claim 5 wherein the sucrose fatty acid polyester is a member selected from the group consisting of the hexaoleate, heptaoleate and octaoleate of sucrose, and mixtures thereof.]

[7. A composition according to claim 1 wherein the anti-anal leakage agent is a member selected from the group consisting of: edible $C_{12}$ and higher saturated fatty acids, and their edible salts; edible, digestible sources of $C_{12}$ and higher saturated fatty acids; edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and edible, non-digestible esters of alpha-branched chain $C_{10}$–$C_{18}$ fatty acids.]

8. A composition according to claim [7] *1* which comprises at least about 10% by weight of the anti-anal leakage agent.

9. A composition according to claim [7] *1* which comprises at least about 20% by weight of the anti-anal leakage agent.

10. A composition according to claim [7] *1* which comprises from about 20% to about 50% by weight of the anti-anal leakage agent.

11. A composition according to claim [7] *1* which comprises from about 10% to about 50% by weight of an anti-anal leakage agent selected from the group consisting of edible $C_{12}$–$C_{24}$ saturated fatty acids and edible salts of $C_{12}$–$C_{24}$ saturated fatty acids.

12. A composition according to claim [7] *1* which comprises from about 10% to about 50% by weight of an anti-anal leakage agent selected from the group consisting of edible, digestible sources of $C_{12}$–$C_{24}$ saturated fatty acids, and mixtures thereof, *other than tristearin or $C_{18}$ saturated fatty acid esters of 1,3-propanediol.*

13. A composition according to claim 12 wherein the anti-anal leakage agent is a lower alkyl ester of $C_{12}$–$C_{24}$ saturated fatty acids, or mixtures thereof.

14. A composition according to claim 12 wherein the anti-anal leakage agent comprises substantially saturated triglyceride esters of $C_{12}$–$C_{24}$ fatty acids, or mixtures thereof, *other than tristearin.*

15. A composition according to claim 14 wherein the anti-anal leakage agent is hydrogenated palm oil.

16. A composition according to claim 14 wherein the anti-anal leakage agent is natural or synthetic cocoa butter.

17. A composition according to claim 14 wherein the anti-anal leakage agent is an edible position-specific triglyceride selected from the group consisting of: the 1-stearoyl, 1-palmitoyl, 1-arachidoyl and 1-behenoyl 2,3-dioleins; the 2-oleoyl 1,3-distearins, 1,3-dipalmitins, 1,3-diarachidins and 1,3-dibehenins; 1-oleoyl distearin; 1-palmitoyl distearin; 1-arachidoyl distearin; and 1-behenoyl distearin; and mixtures thereof.

18. A composition according to claim 17 which comprises from about 20% to about 40% by weight of the position-specific triglyceride.

19. A composition according to claim [7] *1* which comprises from about 20% to about 50% by weight of an anti-anal leakage agent selected from the group consisting of edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group [has] *is a saturated fatty acid group having* from about [8] *10* to about 22 carbon atoms.

20. A composition according to claim 19 wherein the anti-anal leakage agent is selected from the group consisting of [$C_{10}$–$C_{22}$ saturated fatty acid polyol esters] *sucrose octastearate, sucrose octapalmitate, sucrose heptastearate, xylitol pentastearate and galactose pentapalmitate.*

21. A method for inhibiting the absorption of cholesterol in animals without causing an anal leakage effect comprising systemically administering to an animal susceptible to or afflicted with hypercholesterolemia successive therapeutically effective doses of a composition comprising: a non-absorbable, non-digestible liquid polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms and sufficient anti-anal leakage agent to prevent leakage of said liquid polyester through the anal sphincter.

22. A method according to claim 21 wherein the anti-anal leakage agent is a member selected from the group consisting of: edible $C_{12}$–$C_{24}$ saturated fatty acids, and their edible salts; edible, digestible sources of $C_{12}$–$C_{24}$ saturated fatty acids; edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and edible, non-digestible esters of alpha-branched chain $C_{10}$–$C_{18}$ fatty acids.

23. A method according to claim 22 wherein the composition comprises at least about 10% by weight of the anti-anal leakage agent.

24. A method according to claim 23 wherein the composition comprises at least about 20% by weight of the anti-anal leakage agent.

25. A low calorie fat-containing food composition comprising non-fat ingredients and fat ingredients, wherein from about 10% to about 100% of the total fat ingredients comprise:

(a) a portion comprising an edible, non-absorbable, non-digestible liquid polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and (b) sufficient anti-anal leakage agent, *other than tristearin or $C_{18}$ saturated fatty acid esters of 1,3-propanediol,* to prevent leakage of said liquid polyester through the anal sphincter.

26. A composition according to claim 25 wherein the liquid polyol fatty acid polyester contains no more than about 2 free hydroxyl groups.

27. A composition according to claim 26 wherein the fatty acid ester groups contain from about 14 to about 18 carbon atoms.

28. A composition according to claim 27 wherein the polyol is a member selected from the group consisting of erythritol, xylitol, sorbitol, glucose and sucrose.

[29. A composition according to claim 28 wherein the polyol is sucrose.]

[30. A composition according to claim 29 wherein the sucrose fatty acid polyester is a member selected from the group consisting of the hexaoleate, heptaoleate and octaoleate of sucrose, and mixtures thereof.]

31. A composition according to claim 25 wherein the anti-anal leakage agent is a member selected from the group consisting of: edible $C_{12}$ and higher saturated fatty acids, and their edible salts; edible, digestible sources of $C_{12}$ and higher saturated fatty acids, *other than tristearin or $C_{18}$ saturated fatty acid esters of 1,3-propanediol*; edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and edible, non-digestible esters of alpha-branched chain $C_{10}$–$C_{18}$ fatty acids.

32. A composition according to claim 31 wherein the liquid polyester portion of the fat ingredients comprises at least about 10% by weight of the anti-anal leakage agent.

33. A composition according to claim 32 wherein the liquid polyester portion of the fat ingredients comprises at least about 20% by weight of the anti-anal leakage agent.

34. A composition according to claim 33 wherein the liquid polyester portion of the fat ingredients comprises from about 20% to about 50% by weight of the anti-anal leakage agent.

35. A composition according to claim 31 wherein the liquid polyester portion of the fat ingredients comprises from about 10% to about 50% by weight of an anti-anal leakage agent selected from the group consisting of edible $C_{12}$–$C_{24}$ saturated fatty acids and edible salts of $C_{12}$–$C_{24}$ fatty acids.

36. A composition according to claim 31 wherein the liquid polyester portion of the fat ingredients comprises from about 10% to about 50% by weight of an anti-anal leakage agent selected from the group consisting of edible, digestible sources of $C_{12}$–$C_{24}$ saturated fatty acids, and mixtures thereof, *other than tristearin or $C_{18}$ saturated fatty acid esters of 1,3-propanediol.*

37. A composition according to claim 36 wherein the anti-anal leakage agent is a lower alkyl ester of $C_{12}$–$C_{24}$ saturated fatty acids, or mixtures thereof.

38. A composition according to claim 36 wherein the anti-anal leakage agent comprises substantially saturated triglyceride esters of $C_{12}$–$C_{24}$ fatty acids, or mixtures thereof, *other than tristearin.*

39. A composition according to claim 38 wherein the anti-anal leakage agent is hydrogenated palm oil.

40. A composition according to claim 38 wherein the anti-anal leakage agent is natural or synthetic cocoa butter.

41. A composition according to claim 38 wherein the anti-anal leakage agent is an edible position-specific triglyceride selected from the group consisting of: the 1-stearoyl, 1-palmitoyl, 1-arachidoyl and 1-behenoyl 2,3-dioleins; the 2-oleoyl 1,3-distearins, 1,3-dipalmitins, 1,3-diarachidins and 1,3-dibehenins; 1-oleoyl distearin; 1-palmitoyl distearin; 1-arachidoyl distearin; and 1-behenoyl distearin; and mixtures thereof.

42. A composition according to claim 41 wherein the liquid polyester portion of the fat ingredients comprises from about 20% to about 40% by weight of the position-specific triglyceride.

43. A composition according to claim 31 wherein the liquid polyester portion of the fat ingredients comprises from about 20% to about 50% by weight of an anti-anal leakage agent selected from the group consisting of edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms.

44. A composition according to claim 43 wherein the anti-anal leakage agent is selected from the group consisting of $C_{10}$–$C_{22}$ saturated fatty acid polyol esters.

45. A pharmaceutical composition in effective unit dosage amounts for inhibiting the absorption of cholesterol without causing an anal leakage effect, comprising:

a. from about 0.1 gram to about 5 grams of an edible, non-absorbable, non-digestible liquid polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and b. sufficient anti-anal leakage agent to prevent leakage of said liquid polyester through the anal sphincter.

46. A composition according to claim 45 wherein the liquid polyol fatty acid polyester contains no more than about 2 free hydroxyl groups.

47. A composition according to claim 46 wherein the fatty acid ester groups contain from about 14 to about 18 carbon atoms.

48. A composition according to claim 47 wherein the polyol is a member selected from the group consisting of erythritol, xylitol, sorbitol, glucose and sucrose.

49. A composition according to claim 48 wherein the polyol is sucrose.

50. A composition according to claim 49 wherein the sucrose fatty acid polyester is a member selected from the group consisting of the hexaoleate, heptaoleate and octaoleate of sucrose, and mixtures thereof.

51. A composition according to claim 45 wherein the anti-anal leakage agent is a member selected from the group consisting of: edible $C_{12}$ and higher saturated fatty acids, and their edible salts; edible, digestible sources of $C_{12}$ and higher saturated fatty acids; edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and edible, non-digestible esters of alpha-branched chain $C_{10}$–$C_{18}$ fatty acids.

52. A composition according to claim 51 which comprises at least about 10% by weight of the anti-anal leakage agent.

53. A composition according to claim 51 which comprises at least about 20% by weight of the anti-anal leakage agent.

54. A composition according to claim 51 which comprises from about 20% to about 50% by weight of the anti-anal leakage agent.

55. A composition according to claim 51 which comprises from about 10% to about 50% by weight of an anti-anal leakage agent selected from the group consisting of edible $C_{12}$–$C_{24}$ saturated fatty acids and edible salts of $C_{12}$–$C_{24}$ fatty acids.

56. A composition according to claim 51 which comprises from about 10% to about 50% by weight of an anti-anal leakage agent selected from the group consisting of edible, digestible sources of $C_{12}$–$C_{24}$ saturated fatty acids, and mixtures thereof.

57. A composition according to claim 56 wherein the anti-anal leakage agent is a lower alkyl ester of $C_{12}$–$C_{24}$ saturated fatty acids, or mixtures thereof.

58. A composition according to claim 56 wherein the anti-anal leakage agent comprises substantially saturated triglyceride esters of $C_{12}$–$C_{24}$ fatty acids, or mixtures thereof.

59. A composition according to claim 58 wherein the anti-anal leakage agent is hydrogenated palm oil.

60. A composition according to claim 58 wherein the anti-anal leakage agent is natural or synthetic cocoa butter.

61. A composition according to claim 58 wherein the anti-anal leakage agent is an edible position-specific triglyceride selected from the group consisting of: the 1-stearoyl, 1-palmitoyl, 1-arachidoyl and 1-behenoyl 2,3-dioleins; the 2-oleoyl 1,3-distearins, 1,3-dipalmitins, 1,3-diarachidins and 1,3-dibehenins; 1-oleoyl distearin; 1-palmitoyl distearin; 1-arachidoyl distearin; and 1-behenoyl distearin; and mixtures thereof.

62. A composition according to claim 61 which comprises from about 20% to about 40% by weight of the position-specific triglyceride.

63. A composition according to claim 51 which comprises from about 20% to about 50% by weight of an anti-anal leakage agent selected from the group consisting of edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms.

64. A composition according to claim 63 wherein the anti-anal leakage agent is selected from the group consisting of $C_{10}$–$C_{22}$ saturated fatty acid polyol esters.

*65. A composition according to claim 12 wherein said edible sources of saturated fatty acids have an iodine value of from about 9.8 to about 50.*

*66. A composition according to claim 36 wherein said edible sources of saturated fatty acids have an iodine value of from about 9.8 to about 50.*

*67. A composition of matter, comprising:*

*(a) an edible, non-absorbable, non-digestible liquid polyol fatty acid polyester having at least 4 fatty acid ester groups, wherein the polyol is sucrose and wherein each fatty acid group has from about 8 to about 22 carbon atoms; and*

*(b) sufficient anti-anal leakage agent to prevent leakage of said liquid polyester through the anal sphincter, wherein the anti-anal leakage agent is a member selected from the group consisting of: edible $C_{12}$ and higher saturated fatty acids, and their edible salts; edible, digestible sources of $C_{12}$ and higher saturated fatty acids; edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group is a saturated fatty acid group having from about 8 to about 22 carbon atoms; and edible, non-digestible esters of alpha-branched chain $C_{10}$–$C_{18}$ fatty acids.*

*68. A composition according to claim 67 wherein the sucrose fatty acid polyester is a member selected from the group consisting of the hexaoleate, heptaoleate and octaoleate of sucrose, and mixtures thereof.*

*69. A composition according to claim 67 which comprises from about 20% to about 50% by weight of an anti-anal leakage agent selected from the group consisting of edible, non-absorbable, non-digestible solid polyol fatty acid polyesters having at least 4 fatty acid ester groups, wherein the polyol is sucrose and wherein each fatty acid group is a saturated fatty acid group having from about 10 to about 22 carbon atoms.*

*70. A composition according to claim 69 wherein the anti-anal leakage agent is selected from the group consisting of sucrose octastearate, sucrose octapalmitate, and sucrose heptastearate.*

*71. A low calorie fat-containing food composition comprising non-fat ingredients and fat ingredients, wherein from about 10% to about 100% of the total fat ingredients comprise:*

*(a) a portion comprising an edible, non-absorbable, non-digestible liquid polyol fatty acid polyester having at least 4 fatty acid ester groups, wherein the polyol is sucrose and wherein each fatty acid group has from about 8 to about 22 carbon atoms; and*

*(b) sufficient anti-anal leakage agent to prevent leakage of said liquid polyester through the anal sphincter.*

*72. A composition according to claim 71 wherein the sucrose fatty acid polyester is a member selected from the group consisting of the hexaoleate, heptaoleate and octaoleate of sucrose, and mixtures thereof.*

*73. A composition according to claim 71 wherein the liquid polyester portion of the fat ingredients comprises from about 20% to about 50% by weight of an anti-anal leakage agent selected from the group consisting of edible, non-absorbable, non-digestible solid polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms.*

*74. A composition according to claim 73 wherein the anti-anal leakage agent is selected from the group consisting of $C_{10}$–$C_{22}$ saturated fatty acid polyol esters of sucrose.*

*75. A composition according to claim 74 wherein the anti-anal leakage agent is selected from the group consisting of sucrose octastearate, sucrose octapalmitate and sucrose heptastearate.*

*76. A composition of matter, comprising fat ingredients and nonfat ingredients in which at least a portion of the fat ingredients comprise:*

*(a) an edible, non-absorbable, non-digestible liquid polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms; and*

*(b) sufficient anti-anal leakage agent, other than tristearin or $C_{18}$ saturated fatty acid esters of 1,3-propanediol, to prevent leakage of said liquid polyester through the anal sphincter.*

* * * * *

UNITED STATES PATENT AND TRADEMARK OFFICE

CERTIFICATE OF CORRECTION

PATENT NO. : Re. 33,996

DATED : July 14, 1992

INVENTOR(S) : Ronald J. Jandacek and Harry M. Taylor

It is certified that error appears in the above-identified patent and that said Letters Patent is hereby corrected as shown below:

On the title page, item [75]: Inventor: delete "Inventor", and insert --Inventors:--; delete "Cincinnati, Ohio" and insert --; Harry M. Taylor, both of Cincinnati, Ohio--.

In Claim 1, column 12, line 53, "1,3" should be --1,2--.

In Claim 12, column 13, line 42, "1,3" should be --1,2--.

In Claim 25, column 14, line 57, "1,3" should be --1,2--.

In Claim 31, column 15, line 12, "1,3" should be --1,2--.

In Claim 36, column 15, line 46, "1,3" should be --1,2--.

In Claim 76, column 18, line 65, "1,3" should be --1,2--.

Signed and Sealed this

Fourteenth Day of February, 1995

Bruce Lehman

*Attest:*

BRUCE LEHMAN

*Attesting Officer*

*Commissioner of Patents and Trademarks*